United States Patent [19]

Kercso

[11] 3,992,630
[45] Nov. 16, 1976

[54] MEANS FOR SUPPORTING AN OBJECT DURING RADIOGRAPHIC ANALYSIS

[75] Inventor: Josef E. Kercso, Palo Alto, Calif.

[73] Assignee: Syntex (U. S. A.) Inc., Palo Alto, Calif.

[22] Filed: Oct. 15, 1975

[21] Appl. No.: 622,558

[52] U.S. Cl. .......................... 250/360; 250/445 T; 250/491
[51] Int. Cl.² ................. G01N 21/34; G01N 21/00; G01N 23/00; G01N 23/04
[58] Field of Search ................ 250/360, 445 T, 491, 250/456

[56] References Cited
UNITED STATES PATENTS
3,867,634  2/1975  Hounsfield ..................... 250/360

Primary Examiner—Alfred E. Smith
Assistant Examiner—T. N. Grigsby
Attorney, Agent, or Firm—Joseph I. Hirsch; William B. Walker

[57] ABSTRACT

Means for supporting an object, or a portion thereof, during radiographic analysis comprising a hollow reservoir adapted to receive and hold a constant volume of fluid material within the interior thereof, said reservoir having a pouch-like flexible member forming all or a portion of one wall thereof, said pouch-like flexible member being adapted to receive and support the object undergoing analysis during radiographic exposure thereof, a second flexible member forming all or a portion of a second wall thereof, and means operatively connected to said second flexible member for moving said second flexible member so as to cause a corresponding movement of said pouch-like flexible member. During use, the second flexible member is moved in such a manner as to cause an enlargement of the pouch-like deformation of the pouch-like flexible member. After the object to be examined is inserted in the enlarged deformation, the second flexible member is moved so as to cause the pouch-like flexible member to conform to the exterior surface of the object and thereby provide proper support therefor during the radiographic procedure.

18 Claims, 5 Drawing Figures

U.S. Patent   Nov. 16, 1976   Sheet 1 of 2   3,992,630
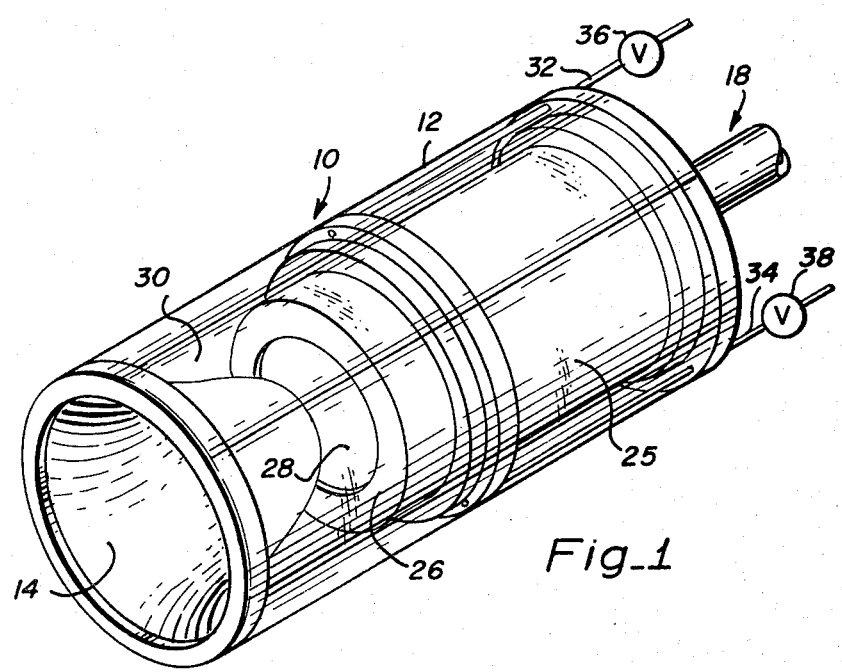
Fig_1
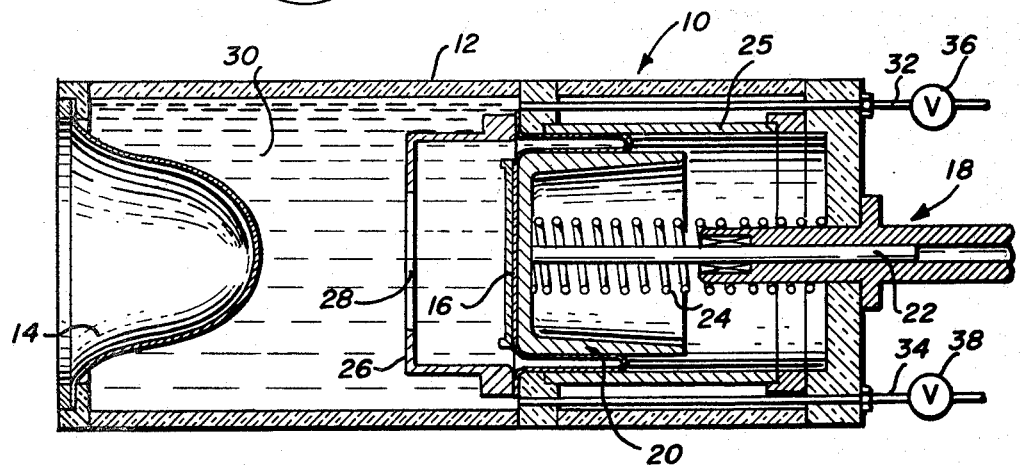
Fig_2
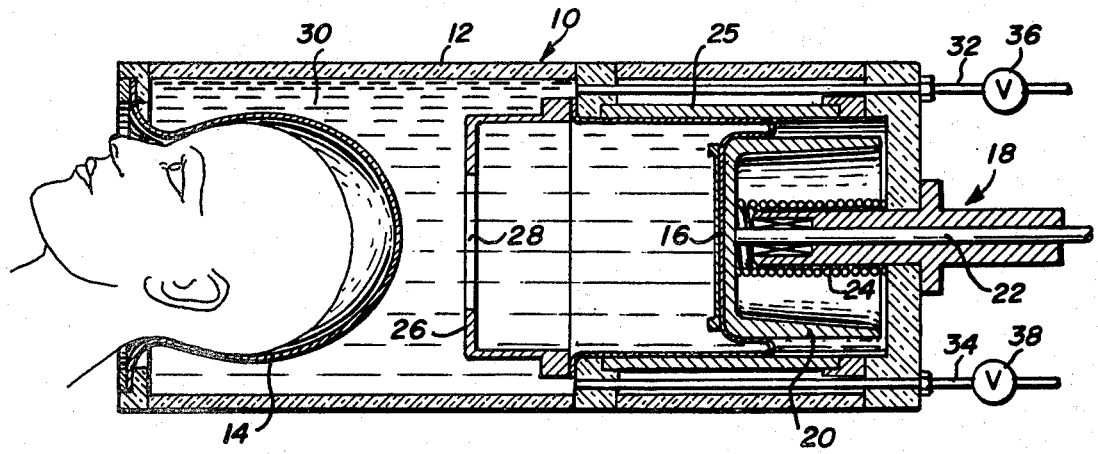
Fig_3

MEANS FOR SUPPORTING AN OBJECT DURING RADIOGRAPHIC ANALYSIS

FIELD OF THE INVENTION

This invention relates to means for supporting an object during radiographic analysis. More particularly, this invention relates to means for supporting a portion of the human body, such as the head, during radiographic analysis thereof, for example with X-rays by means of a computerized axial tomographic scanner. Known means for providing such support, through use of a device having a distinctly different structure, is shown by Hounsfield U.S. Pat. No. 3,867,634.

BRIEF SUMMARY OF THE INVENTION

The support means of the present invention comprises a hollow reservoir adapted to receive and hold a constant volume of fluid material within the interior thereof; said reservoir having a pouch-like flexible member forming all or a portion of one wall thereof, said pouch-like flexible member being adapted to receive and support the object undergoing analysis during radiographic exposure thereof; a second flexible member forming all or a portion of a second wall thereof; and means connected to said second flexible member for moving said second flexible member so as to cause a corresponding movement of said pouch-like flexible member.

In a specific embodiment, for example as shown in FIGS. 1–3 hereof, the reservoir comprises a right cylinder having a rigid side wall, a pouch-like flexible member forming one end wall thereof, a second flexible member forming the other end wall thereof and mechanical means for moving the second flexible member to cause a corresponding movement of the pouch-like flexible member which is adapted to receive and hold the object undergoing radiographic analysis.

Upon actuation of the means for moving the second flexible member, generally along the longitudinal axis of the housing in a direction away from the pouch-like flexible member, the pouch-like flexible member is bowed inwardly of the reservoir to an extent depending upon the degree of movement of the second flexible member and the actual configuration of the reservoir. In this position, an object, e.g., a body part, such as a head, can be inserted into the relatively larger deformation now occuring in the pouch-like flexible member. After appropriate positioning of the object, as by a physician or technician, the second flexible member is moved, generally inwardly, so as to cause the pouch-like flexible member to conform to the exterior surface of the object and thereby provide proper support therefor during the radiographic procedure.

In a further specific embodiment, for example as shown in FIGS. 4 and 5 hereof, the reservoir comprises a right cylinder having a rigid side wall, a pouch-like flexible member forming one end wall thereof, a second flexible member forming the other end wall thereof, and vacuum means, as opposed to mechanical means, for moving the second flexible member to cause a corresponding movement of the pouch-like flexible member which is adapted to receive and hold the object undergoing radiographic analysis. The vacuum means can be, for example, a rigid, cap-like, extension means adapted to be secured in an air-tight manner to that end of the housing adjacent the second flexible member. The extension means is connected to a vacuum pump or other means adapted to create a vacuum in the space between the second flexible member and the wall(s) of the extension member. The extension member is of sufficient longitudinal dimension to permit the desired extension of the second flexible member when a vacuum is created within the space between the second flexible member and the wall(s) of the extension member. The extension member can also be opened to the atmosphere (and less desirably to a source of pressurized air or gas) to reduce, or totally eliminate, the vacuum created in the extension member and thus cause the pouch-like flexible member to substantially return to its initial position (i.e., to the object-supporting position).

Upon creation of a vacuum in the extension member, the second flexible member will move, generally along the longitudinal axis of the housing in a direction away from the pouch-like flexible member, and this will cause a corresponding movement of the pouch-like flexible member inwardly of the reservoir to an extent depending upon the degree of movement of the second flexible member and the actual configuration of the reservoir. In this position, an object can be inserted into the relatively larger deformation now occuring in the pouch-like flexible member. After appropriate positioning of the object, the vacuum in the extension member is gradually reduced whereby the second flexible member will move inwardly so as to cause the pouch-like flexible member to conform to the exterior surface of the object and thereby provide proper support therefor during the radiographic procedure.

Additional means can be provided adjacent the pouch-like flexible member for providing a constant attenuation path for the radiation beams used for the radiographic analysis. For example, a rectangular plastic block having a circular opening therein can be positioned about that end of the housing adjacent the pouch-like flexible member. The plastic material, from which the block is fabricated, should have an attenuation equivalent, or substantially equivalent, to water thereby assuring, as set forth above, that a constant attenuation path will be provided for the radiation beams.

In a further aspect of the invention, the support means described herein is utilized in conjunction with a diagnostic radiographic instrument, such as, for example, a computerized axial tomographic scanner. Such a scanner, in one configuration thereof, has a source of X-rays or γ-rays adapted to transmit a beam of radiation through a slice of the object to be examined, detector means to detect the transmitted beam after it has passed through the object, and means to sequentially translate and rotate the source and detector means about the object during the radiographic examination. Such a scanner is shown, for example, by U.S. Pat. No. 3,778,614. In a different configuration, as shown by copending application Ser. No. 528,026, filed Nov. 29, 1974, in the name of Douglas Boyd et al, a fan-shaped beam of penetrating radiation is directed through the slice of the object to be analyzed to a radiation-sensitive detector for deriving a set of data corresponding to the transmission or absorption of the penetrating radiation by the object along a plurality of divergent lines extending from the source to the detector. A number of sets of such data are obtained for different angles of rotation of the fan-shaped beam relative to the center of the slice being analyzed. The principal difference between this configuration, and the preceeding configuration, is that in this configuration there is no lateral translation of the source and the detector, rather the source and detector need only be rotated about the object undergoing examination to provide sufficient sets of data to permit the necessary reconstruction of the particular slice being examined. The supporting means of the present invention can be utilized in conjunction with either of the aforesaid configurations, other computerized axial tomographic configurations which may differ from the above configurations, or other X-ray or γ-ray diagnostic apparatus and configurations which require means for supporting an object, such as a body part, during the radiographic examination. U.S. Pat. No. 3,778,614 and copending application Ser. No. 528,026, filed Nov. 29, 1974, are incorporated herein by reference to the extent necessary to complete, or render fully understandable, the disclosure hereof.

BRIEF DESCRIPTION OF THE DRAWINGS

The features and advantages of the present invention will become more apparent from the following detailed description, taken together with the accompanying drawings wherein:

FIG. 1 is a perspective view of one embodiment of the support means of the present invention;

FIG. 2 is a vertical cross-sectional view of the embodiment of FIG. 1 showing the pouch-like flexible member in the relaxed condition (i.e., in a generally non-object supporting position);

FIG. 3 is a further vertical cross-sectional view of the embodiment of FIG. 1 showing the pouch-like flexible member deformed to an enlarged, object-receiving position;

Referring to FIGS. 1–3, there is shown a support means 10 having a generally transparent reservoir means 12, for example, a rigid right-cylinder as shown. It should be understood, however, that reservoir 12 can be of other shapes and configurations than the right-cylinder as shown in the figures. At one end of the reservoir 12, there is a pouch-like flexible member 14 which is adapted to receive and hold the object to be examined during radiographic analysis thereof. At the other end of the reservoir there is flexible member 16 connected to means, generally designated 18, for moving the flexible member 16 inwardly and outwardly of reservoir 12. Such movement is generally along the longitudinal axis of the right-cylinder, although other movements and positioning of flexible member 16 are contemplated to be within the scope of this invention. As shown, means 18 comprises a moveable frame 20 upon which flexible member 16 is supported. Connected to frame 20 is rod 22 surrounded by spring 24 which normally urges frame 20, and thus flexible member 16, toward pouch-like flexible member 14. Cylindrical guide 25 assists in maintaining the longitudinal attitude of frame 20 and the elements associated therewith. The inward movement of frame 20 and flexible member 16 is limited by stop 26 having a central aperture 28 therein. The hollow interior of reservoir 12 between flexible members 14 and 16 is filled with a constant volume of fluid material 30 via inlet line 32 which is closed after the reservoir is completely filled and which remains closed during the object-supporting procedure. Outlet line 34 is also provided for emptying the reservoir, for example to provide a new fluid material and/or clean the interior of the reservoir. Valves 36 and 38 control inlet line 32 and outlet line 34, respectively. It should be understood, however, that inlet line 32 and outlet line 34 are not essential parts of this invention and that the reservoir can be a constant volume fluid container which is completely sealed so the fluid therein cannot be removed therefrom (other than by destruction of one of the walls thereof).

In use, means 18 is moved in a manner which causes flexible member 16 to be moved outwardly of the reservoir from the position shown in FIG. 2 to the position generally shown in FIG. 3. This movement of flexible member 16 causes a corresponding enlargement of the deformation in pouch-like flexible member 14. After the object to be examined, for example the head of a patient, is inserted into the enlarged deformation in pouch-like flexible member 14, flexible member 16 is gradually moved inwardly. This movement of flexible member 16 causes a corresponding movement of pouch-like flexible member 14 whereby the pouch-like member will conform to the exterior surface of the object and thereby provide proper support therefor. After the radiographic procedure is completed, outward movement of flexible member 16, in response to movement of means 18, will cause a corresponding movement of pouch-like flexible member 14, whereby the deformation in pouch-like flexible member will be increased and the supported object can easily be withdrawn therefrom.

Figure 4:
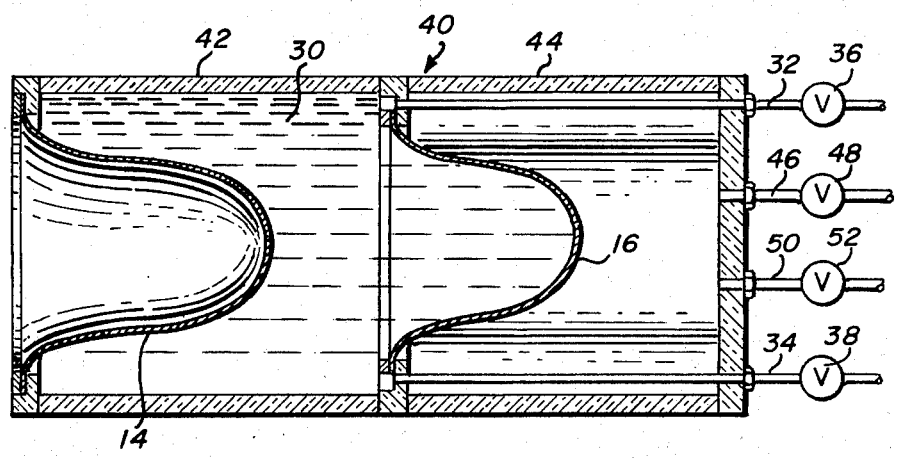
FIG. 4 is a vertical cross-sectional view of an alternate embodiment of the support means of the present invention, showing the pouch-like flexible member as it is being deformed to an enlarged, object-receiving position.
Figure 5:
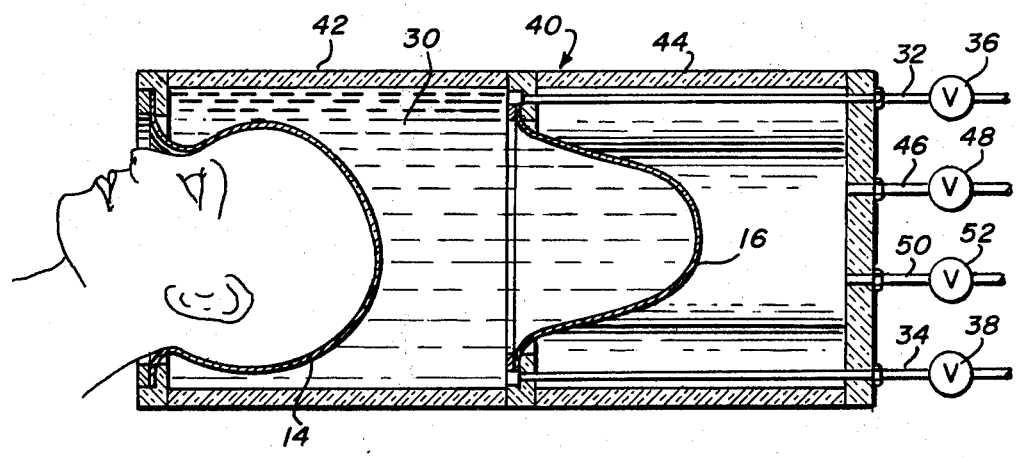
FIG. 5 is a further vertical cross-sectional view of the alternate embodiment of FIG. 4 showing the pouch-like flexible member in the object-supporting position where it has been caused to conform the exterior configuration of the object undergoing radiographic examination.

Referring to FIGS. 4 and 5, where like numbers have been utilized to designate like elements as found in FIGS. 1–3, there is shown support means 40 having a transparent reservoir means 42, for example, a rigid right-cylinder as shown. As with the apparatus of FIGS. 1–3, it should be understood that reservoir 42 can be of a different shape and configuration than the right-cylinder as shown in this figure. At one end of the reservoir 42, there is a pouch-like flexible member 14 which is adapted to receive and hold the object to be examined during the radiographic analysis thereof. At the other end of the reservoir there is a flexible member 16 connected to means, to be described below, for moving the flexible member 16 inwardly and outwardly of reservoir 42. The hollow interior of reservoir 42 between members 14 and 16 is filled with a constant volume of fluid material 30 via inlet valve 32 which can be closed after the reservoir is completely filled and which remains closed during the object-supporting procedure. Drain line 34 is providing for emptying the reservoir, for example to provide new fluid material and/or clean the interior of the reservoir. At the end of reservoir 42 adjacent flexible member 16, there is an air-tight extension member or vacuum chamber 44 connected via conduit 46 and valve 48 to a vacuum pump (not shown). Extension member 44 is also connected via conduit 50 and valve 52 to the atmosphere or, less desirably, to a source (not shown) of air or other pressurized gas. As with the device of FIG. 1, lines 32 and 34 are not an essential part of this configuration as the reservoir can be a constant volume fluid-filled container which is completely filled so the fluid therein cannot be removed therefrom other than by destruction of one of the walls thereof. In use, air is withdrawn from the space between flexible member 44 by means of the vacuum pump via conduit 32. This vacuum causes the deformation in flexible member 16 to be enlarged from its initial size. This movement of flexible member 16 causes a corresponding enlargement of the deformation in pouch-like flexible member 14. After insertion of the object to be analyzed in the enlarged deformation in pouch-like flexible member 14, the vacuum originally created in extension member 44 is decreased, generally by opening extension member 44 to the atmosphere to reduce the vacuum to the desired level. This pressurization causes flexible member 16 to be moved, generally inwardly, so as to cause a corresponding movement of pouch-like flexible member 14 whereby the pouch-like flexible member will conform to the exterior surface of the object undergoing radiographic analysis and thereby provide proper support therefor, as shown in FIG. 5 hereof. After the radiographic procedure is completed, the vacuum is once again created in extension member 44 which will cause movement of flexible member 16, and corresponding movement of pouch-like flexible member 14, whereby the deformation in pouch-like flexible member 14 will be enlarged and the supported object can easily be withdrawn therefrom. If desired, appropriate gauges can be operatively connected to either the hollow reservoir and/or the vacuum chamber to measure the various pressures therein as an aid in comfortably supporting the object (e.g., the head of a patient) without undue pressure being applied to the supported object.

It should be understood that the volume of fluid within the reservoir of either of the embodiments described above is maintained constant during positioning of the object in the pouch-like flexible member, subsequent movement of the pouch-like flexible member into the supporting position prior to radiographic examination thereof, and the radiagraphic examination per se. That is, to achieve object support at the time of use (assuming reservoir 12 or reservoir 42 is completely filled), no liquid or fluid material is added to, or withdrawn from, the space defined by the walls) of the reservoir, the pouch-like flexible member and the second flexible member. The devices of the invention, accordingly, are compact, simple to operate, and do not require bulky supplies of liquid material or flexible conduits adapted to connect the support means with a remote reservoir for the supply of the liquid to be added to, and withdrawn from, the support means during actual object-supporting use. In addition, this device eliminates the need for a rotary-tight seal as shown in U.S. Pat. No. 3,881,110, and permits the use of boiled (sterilized), degassed distilled water which will reduce or eliminate the undesirable growth of algae in the object support mechanism.

While this invention has been described with reference to specific embodiments thereof, it should be understood by those skilled in this art that various changes may be made and equivalents may be substituted without departing from the true spirit and scope of the invention. All such modifications are intended to be within the scope of the claims appended hereto.

What is claimed is:

1. Means for supporting an object, or a portion thereof, during radiographic analysis comprising a hollow reservoir adapted to receive and hold a constant volume of fluid material within the interior thereof, said reservoir having a pouch-like flexible member forming all or a portion of one wall portion thereof, said pouch-like flexible member being adapted to receive and support the object undergoing analysis during radiographic exposure thereof, a second flexible member forming all or a portion of a second wall portion thereof, and vacuum means for moving said second flexible member so as to cause a corresponding movement of said pouch-like flexible member.

2. The support means of claim 1 wherein said hollow reservoir comprises a right cylinder having a rigid side wall, said pouch-like flexible member forms one end wall of said right cylinder, and said second flexible member forms the other end wall of said right cylinder.

3. The support means of claim 1 wherein said pouch-like flexible member has a deformation therein and said vacuum means for moving said second flexible member comprises vacuum chamber means adjacent to said second flexible member and in air-tight engagement with said reservoir, said vacuum chamber means adapted to be connected to vacuum source means for creating a vacuum therein, whereby, upon creation of a vacuum in said vacuum chamber means, the deformation in said pouch-like flexible member is sufficiently enlarged to receive the object to be analyzed, and, upon at least partial elimination of the vacuum in said vacuum chamber means, said pouch-like flexible member conforms to the exterior surface of the object thereby providing support therefor during the radiographic procedure.

4. The support means of claim 3 wherein said vacuum chamber means includes a hollow extension member attached in airtight engagement to said reservoir.

5. The support means of claim 3 wherein said hollow reservoir comprises a right cylinder having a rigid side wall, said pouch-like flexible member forms one end wall of said right cylinder, said second flexible member forms the other end wall of said right cylinder, and said vacuum chamber means includes a hollow, cylindrical extension member attached in airtight engagement to said right cylinder on the opposite side of said second flexible member from said pouch-like flexible member.

6. The support means of claim 3 further including vacuum source means and means to connect said vacuum source means to said vacuum chamber means.

7. The support means of claim 6 further including means to reduce a vacuum created in said vacuum chamber means.

8. The support means of claim 1 further including a constant volume of fluid within said hollow reservoir.

9. The support means of claim 8 wherein said fluid is water.

10. An axial tomographic system comprising axial tomographic means for collecting a plurality of sets of data corresponding to the transmission or absorption of a plurality of beams of penetrating radiation through a planar slice of an object being analyzed including means to locate an object to be analyzed, source and detector means for directing one or more beams of penetrating radiation through the object from the source to the detector means, and means to rotate the source and detector means about the object whereby a plurality of sets of data corresponding to the transmission or absorption by the object of the plurality of beams of penetration radiation are collected; said means to locate the object including means for supporting the object, or a portion thereof, comprising a hollow reservoir adapted to receive and hold a constant volume of fluid material within the interior thereof, said reservoir having a pouch-like flexible member forming all or a portion of one wall portion thereof, said pouch-like flexible member being adapted to receive and support the object undergoing analysis during radiographic exposure thereof, a second flexible member forming all or a portion of said wall portion thereof, and vacuum means for moving said second flexible member so as to cause a corresponding movement of said pouch-like flexible member.

11. The system of claim 10 wherein said hollow reservoir comprises a right cylinder having a rigid side wall, said pouch-like flexible member forms one end wall of said right cylinder, and said second flexible member forms the other end wall of said right cylinder.

12. The system of claim 10 wherein said pouch-like flexible member has a deformation therein and said vacuum means for moving said second flexible member comprises vacuum chamber means adjacent to said second flexible member and in air-tight engagement with said reservoir, said vacuum chamber means adapted to be connected to vacuum source means for creating a vacuum therein, whereby, upon creation of a vacuum in said vacuum chamber means, the deformation in said pouch-like flexible member is sufficiently enlarged to receive the object to be analyzed, and, upon at least partial elimination of the vacuum in said vacuum chamber means, said pouch-like flexible member conforms to the exterior surface of the object thereby providing support therefor during the radiographic procedure.

13. The system of claim 10 wherein said vacuum chamber means includes a hollow extension member attached in air-tight engagement to said reservoir.

14. The system of claim 10 wherein said hollow reservoir comprises a right cylinder having a rigid side wall, said pouch-like flexible member forms one end wall of said right cylinder, and said second flexible member forms the other end wall of said right cylinder, and said vacuum chamber means includes a hollow, cylindrical extension member attached in air-tight engagement to said right cylinder on the opposite side of said second flexible member from said pouch-like flexible member.

15. The system of claim 10 further including vacuum source means and means to connect said vacuum source means to said vacuum chamber means.

16. The system of claim 15 further including means to reduce a vacuum created in said vacuum chamber means.

17. The system of claim 10 further including a constant volume of fluid within said hollow reservoir.

18. The system of claim 17 wherein said fluid is water.

* * * * *